US008728542B2

(12) United States Patent
Pickardt et al.

(10) Patent No.: US 8,728,542 B2
(45) Date of Patent: May 20, 2014

(54) PROTEIN PREPARATIONS FROM SUNFLOWER SEEDS AND PRODUCTION THEREOF

(75) Inventors: Claudia Pickardt, Berlin (DE); Peter Eisner, Freising (DE); Stephanie Bader, Freising (DE); Florian Wild, Freising (DE); Klaus Muller, Freising (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 13/202,770

(22) PCT Filed: Feb. 26, 2010

(86) PCT No.: PCT/EP2010/001222
§ 371 (c)(1),
(2), (4) Date: Sep. 27, 2011

(87) PCT Pub. No.: WO2010/097238
PCT Pub. Date: Sep. 2, 2010

(65) Prior Publication Data
US 2012/0009287 A1    Jan. 12, 2012

(30) Foreign Application Priority Data
Feb. 27, 2009   (DE) .......................... 10 2009 010 813

(51) Int. Cl.
*A01N 65/00*   (2009.01)
(52) U.S. Cl.
USPC ....................................................... 424/725
(58) Field of Classification Search
None
See application file for complete search history.

(56) References Cited

U.S. PATENT DOCUMENTS

| | | | | |
|---|---|---|---|---|
| 3,356,518 A | * | 12/1967 | Gilboe et al. | 106/155.23 |
| 3,734,901 A | | 5/1973 | Hayes et al. | |
| 4,219,469 A | | 8/1980 | Kadan et al. | 260/123.5 |
| 4,219,470 A | | 8/1980 | Karnofsky | 260/123.5 |
| 4,889,921 A | * | 12/1989 | Diosady et al. | 530/377 |

FOREIGN PATENT DOCUMENTS

| | | | |
|---|---|---|---|
| GB | 1 502 959 | 3/1978 | ............... C07G 7/00 |
| WO | WO 04/000032 A2 | 12/2003 | ............... A23J 1/14 |

OTHER PUBLICATIONS

International Search report in corresponding application No. PCT/EP2010/001222 mailed Aug. 24, 2010.
*Obtencion de harina y de un concentrado proteninico a partir de semillas de heliantus annus y su incorporacion en galletas*; Bourges et al.; Archivos LatinoAmericanos De Nutricion; vol. 30, No. 4.; 1980; pp. 564-579; XP009135815.
*Sunflower protein concentrates and isolates low in polyphenols and phytate.* ; Saeed et al.; Journal of Food Science; vol. 53, No. 4; Jul. 1988, pp. 1127-1131; XP002590909.
*Preparation and application of vegetable proteins, especially proteins from sunflower seed, for human consumption. An Approach.*; Gassman; Nahrung; vol. 27, No. 4; 1983; pp. 351-369; XP002590910.
*Almost complete dehulling of high oil sunflower seed.*; Tranchino et al.; Journal of The American Oil Chemists' Society; vol. 61, No. 7, Jul. 1984; pp. 1261-1265; XP002590911.
*A process for the dehulling of high-oil content sunflower seeds.*; Miller et al.; Fette Seifen Anstrichmittel; vol. 88, No. 7; 1986, pp. 268-271; XP002590912.
*Certain Functional Properties of Sunflower Meal Products*; Lin; Journal of Food Science [On Line]; vol. 39, No. 2; 1974—1974; pp. 368-370 (http://www3.interscience.wiley.com/cgi-bin/fulltext/119662970/PDFSTATR?CRETRY=1&SRETRY=0>); XP002590913.
*Sunflower seeds and products of their processing. I. Production and value-determining constituents.* (Translated); Mieth et al.; Die Nahrung; vol. 28, No. 5; 1985; pp. 533-577; XP002590914.

* cited by examiner

*Primary Examiner* — Michael Meller
(74) *Attorney, Agent, or Firm* — Renner Kenner Greive Bobak Taylor & Weber

(57) ABSTRACT

The present invention relates to a method of obtaining protein preparations from sunflower seeds as well as protein preparations produced with the method. In the method the sunflower seeds are dehulled to a residual hull content of ≤5% by weight or dehulled sunflower seeds with a residual hull content of ≤5% by weight are provided. Mechanical partial deoiling of the dehulled sunflower seeds is carried out through pressing up to a fat or oil content of the dehulled sunflower seeds in the range 10 to 35% by weight. After carrying out one or more extraction steps with at least one solvent, a defatted flour containing protein is obtained as a protein preparation. Both optically and functionally the protein preparation has very advantageous properties which allow it to be used directly in the food product or animal feed sector.

13 Claims, 2 Drawing Sheets

PROTEIN PREPARATIONS FROM SUNFLOWER SEEDS AND PRODUCTION THEREOF

TECHNICAL FIELD OF APPLICATION

The present invention relates to a method of obtaining protein preparations from sunflower seeds as well as protein preparations produced with this method that have improved usage properties.

PRIOR ART

Protein preparations are widely used in food products as nutritional physiological or techno-functional additives. There are protein preparations with a particularly high protein value for use as high-grade food additives (baby food, special food, sports nutrition). In principle these are also of interest for the formulation of animal feeds which have to guarantee a high degree of protein availability. Other protein preparations exhibit good technofunctional properties and are suitable, for example, for stabilising foams or emulsions or to produce gels. These protein preparations are supremely suitable as food additives and are also used for special feeds or technical purposes.

Fundamentally, protein preparations of animal and plant origin can be distinguished. Examples of protein preparations of animal origin are those produced from hen eggs, milk, whey or casein and gelatine products from abattoir waste. The disadvantage is that such protein products have their own characteristic taste and smell as a result of which they are restricted to certain uses. They are often expensive to produce and are problematical in terms of allergies, and they are rejected by certain consumers on ethical grounds.

In the case of plant protein preparations a distinction is made between protein concentrates and protein isolates on the basis of their production. In comparison with plant protein concentrates with a protein content of between 60% and 90%, protein isolates have a very high protein content of at least 90%. To produce protein isolates the proteins are dissolved in water and then isolated from the aqueous solution. Compared with the extracted plant seeds they have a modified amino acid profile and modified nutritional and technofunctional properties.

The main plant protein preparations on the market are soya protein preparations, namely soya protein concentrates and isolates and wheat gluten preparations. In addition, protein preparations from other leguminous proteins, such as pea protein concentrates, are available.

Also known on the market as plant protein preparations are mainly protein concentrates and protein isolates from deoiled oil seeds, such as rape seeds and sunflower seeds. At present these are used almost exclusively for the production of oil. In contrast to soya the resulting pressing and extraction residues (oil cakes and grist) have so far not been used in the food sector in spite of their high nutritional functional and techno-functional potential. One reason for this is the proportion of troublesome secondary substances such as polyphenols which can impair the taste and the colour of the products.

In accordance with the prior art oil seeds and legumes are deoiled with hexane. Legume seeds are peeled, flaked and undergo extraction with hexane in an extraction installation. Oils seeds are either flaked and directly deoiled or mechanically partially deoiled (pre-pressing) and completely deoiled through extraction, whereby the oil cake has to be broken up before extraction in order to allow the extraction to take place. Complete pressing up to a residual oil content of approximately 5% without subsequent extraction is also carried out, whereby the residual oil content in the expellers (oil cakes, grist) reduces the storage stability.

Hitherto sunflower seeds have mainly been used whole or max. ⅔ dehulled for deoiling. More particularly, for pressing, i.e. complete pressing or pre-pressing as partial deoiling, a high hull content is considered to be necessary. The oil cakes and grist are dark in these cases and have a very high raw fibre content. They are not therefore suitable for producing high-value protein flours and concentrates.

There are various ways of isolating proteins from residues from the production of sunflower oil. At the forefront of this is the removal of the problematic polyphenols, principally chlorogenic acid, which impair the colour of sunflower protein isolates. To date extraction with various solvents, including water and alcohols has been proposed for removing the polyphenols from deoiled sunflower grist. Obtaining protein isolates from sunflower seeds and oil cakes or grist is particularly difficult due to the low solubility of sunflower proteins which requires the use of alkali or salts. This involves a particularly high level of water consumption for protein preparation (washing), associated with high protein losses, which increases the production costs of the protein isolate and thereby reduces their range of application.

To remove the colour-active phenolic substances from deoiled sunflower seeds with the aim of subsequent protein extraction and the obtaining of protein isolates from the thus pre-treated material, various aqueous alcoholic mixtures have been tested, more particularly butanol in various proportions with water containing hydrochloric acid, ethanol at a proportion of 95% (v/v), isopropanol (70% v/v) and methanol (80% v/v). The disadvantage of extraction with these solvents is the extensive denaturing of the proteins through the solvent treatment so that the protein solubility is sharply decreased. As a result the subsequent extraction of proteins in the production protein isolates as well their functional properties are greatly restricted.

WO02/060273A1 describes a method with which protein isolates with a protein content of more than 90% are obtained from sunflower seeds. For this, the proteins are extracted in an aqueous manner and obtained by precipitation with alcohol at low temperatures. These are expensive due to the high energy consumption for the cooling and therefore restricted in their application.

Protein concentrates from sunflower seeds are obtained through dry and wet processing, whereby the protein remains in the residue. The high proportion of undesirable secondary substances restricts their use in the food sector. Overall the known plant protein concentrates with a low level of purification are restricted in terms of their functional properties and/or contain a certain proportion of troublesome components which can have a very negative effect on the nutritional value, colour, smell and/or taste of foods in which they are contained. Protein concentrates from sunflower seeds therefore have a limited range of application and can only be used in low concentrations.

The aim of the present invention is to provide a cost-effective method of producing protein preparations which appeal to the senses and can be widely used.

DESCRIPTION OF THE INVENTION

This aim is achieved with the method in accordance with claim 1. The other claims set out preferred examples of embodiment of the method, a protein preparation that can be produced with the method and its preferred forms of embodiment, as well as a product which can be produced with the protein preparation.

In the proposed method of obtaining the protein preparations from sunflower seed at least the following steps are carried out:

Dehulling of the sunflower seeds to a residual hull content of ≤5% by weight or the provision of dehulled sunflower seeds with a residual hull content of ≤5% by weight (in each case related to the total mass of the seed fraction obtained immediately after dehulling);

Mechanical deoiling of the dehulled sunflower seeds through pressing to a fat or oil content of the dehulled sunflower seeds in a range between 10 and 35% by weight, and Carrying out one or more extraction steps with at least one solvent, through which a deoiled flour containing proteins is obtained as the protein preparation. At least one of the extraction steps in the method is carried out so that further deoiling of the partially deoiled dehulled sunflower seeds is brought about.

Through the combination of the low residual hull content and mechanical partial deoiling to the indicated residual oil content protein concentrates can be obtained which both optically and also functionally have very advantageous properties for use in food products and animal feeds. The method allow particularly gentle treatment of the proteins in that during the mechanical and/or further deoiling too high a temperature is avoided, which could lead to undesirable protein modifications and changes in flavour.

The mechanical deoiling of the sunflower seeds to the indicated residual oil content is preferably carried out so that a mechanically stable oil cake with a thickness in the range 0.2 to 4 cm, preferably in the range 0.2 to 4 cm is obtained. This simplifies the subsequent processing steps as further extraction can be dispensed with due to the porosity and thickness of the oil cake.

The method in accordance with the invention allows gentle production of the preparation in that denaturing of the proteins is permitted in a defined way. The partial deoiling and the one or more extraction steps are carried out in such a manner that the degree of denaturing of the proteins in the deoiled flour containing protein (related to the starting product of the method) is maximum 40%, preferably between 10% and 30%. This allows protein preparations of high qualitative and sensory value with a wide application range to be obtained.

Preferably the extraction is carried out with a solvent or a solvent mixture in several extraction stages comprising a combination of at least one lipophilic extraction stage with a lipophilic solvent or solvent mixture and at least one hydrophilic extraction stage with a hydrophilic solvent or solvent mixture. In addition, the concentration of the extraction solvent in the last extraction stage is preferably increased to such an extent that subsequent drying can take place in a particularly simple and gentle manner.

The protein preparation that can be produced from sunflower seeds using this method has a protein content of at least 50%. Cost-effective production is possible as a high degree of purification, as required in the case of the protein isolate, can be avoided.

Surprisingly, in spite of its high proportion of non-protein substances, the protein preparation exhibits properties which are similar to the known protein isolates produced from these raw materials or are even more versatile than these. Because of the light colour as well as the balanced technofunctional spectrum in the form of hydration, oil-binding and emulsifying functional properties the protein preparation can be widely used, including in food products and animals feed, in order to bind water and/or oil and/or to form an emulsion. The protein preparation is suitable for replacing other preparations which have previously been used for these functions and are of animal or plant origin, such as hen eggs, milk, soya in the form of soya protein isolates etc.

Even in the form of the particularly cost-effectively producible sunflower seed flour, i.e. the deoiled protein-containing flour obtained directly from method, the protein preparation has surprising properties in terms of colour and functional propertes which allow the protein flour to be directly used in numerous food products and animal feeds.

The range of use of the protein preparation can be extended even further if the protein preparation is free of the plant or seed's own aromas, more particularly if it essentially has no smell and/or is essential neutral in taste. This prevents undesirable changes in taste and aroma when the protein preparation is incorporated into food or feed products.

The range of use can also be extended through a foam-forming function so that the protein preparation can be used, for example, as a substitute for egg white or other foam-forming additives in order to produce foam-like food products.

Preferably the protein preparation has a low fat content which ensures good storage stability of the protein preparation.

Preferably the protein preparation also has a low content of phytinic acid, oligosaccharides and/or phenolic acids. In this way the content of substance is reduced which can impair the utilisation of nutritional substances during digestion.

BRIEF DESCRIPTION OF THE DRAWINGS

The proposed production method and the producible protein preparation will be explained again below in more detail in conjunction with the drawings, in which.

WAYS OF IMPLEMENTING THE INVENTION

The method in accordance with the invention can be implemented in the following manner for example. As a starting point preferably edible type sunflower seeds or those that have a light-coloured hull are selected. However, normal and high oleic type sunflower seeds can also be used.

The prepared raw material is extracted successively in an extractor with different solvents under such conditions that no or only very little protein is dissolved. This minimises protein losses and modifications. Particularly advantageous is carrying out solvent extraction with an alcohol, for example ethanol, propanol, isopropanol.

Of course several extraction installations for the various solvents can be used. The same applies to the drying installation.

Figure 1:
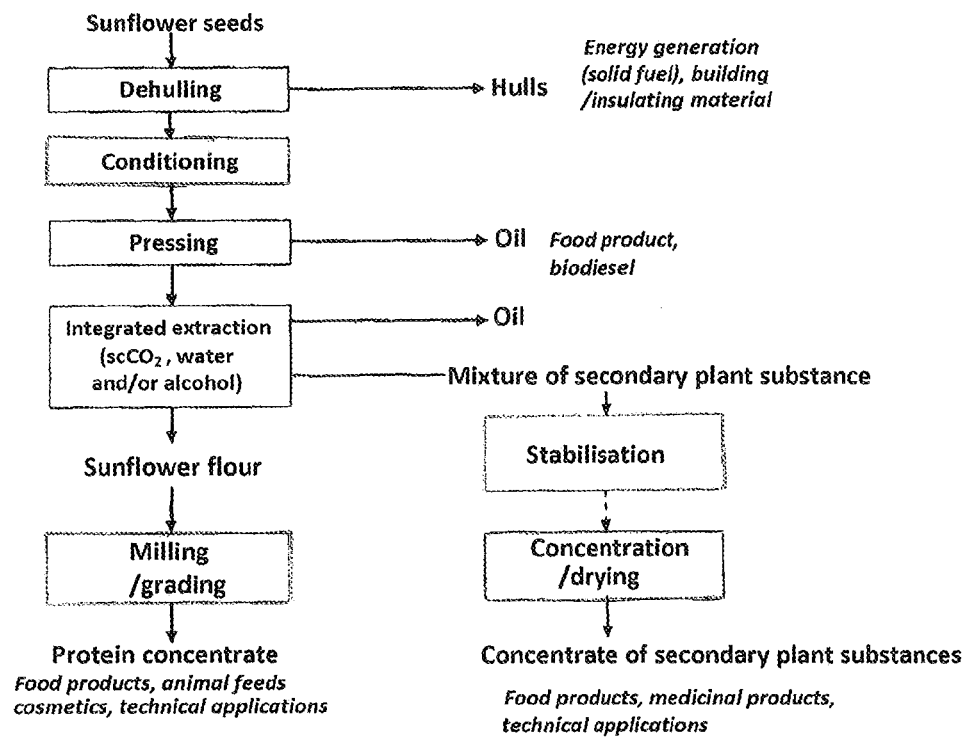
FIG. 1 shows a schematic view of an example of the process sequence of the proposed method with fractionation of the sunflower seeds containing phenolic acid in oil, polyphenols and protein concentrate as well as optional further fractionation into protein isolates; the usage possibilities of the individual fraction are indicated in italics.
Figure 3:
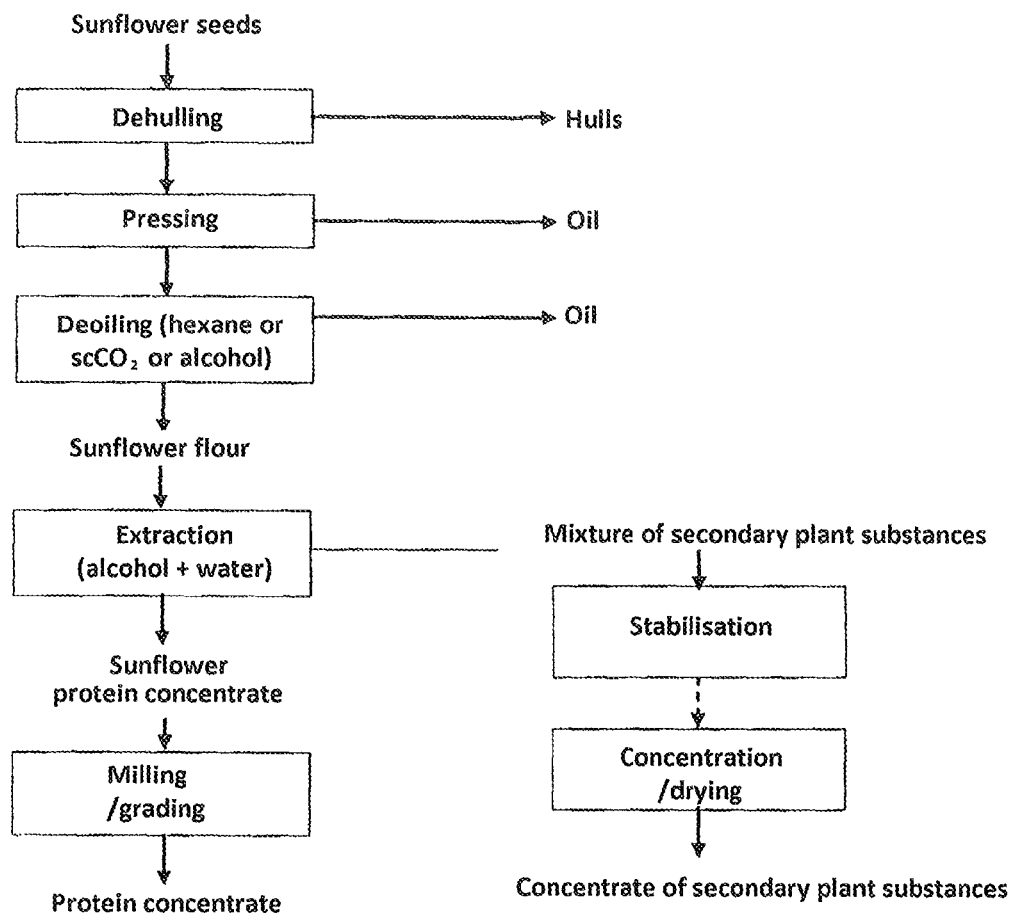
FIG. 3 schematically shows a further example of the processing sequence of the proposed methods with the stage dehulling, pressing and hexane extraction (alternatively: deoiling with $scCO_2$ or with alcohol), subsequent alcohol-water extraction, alcohol-water displacement drying and subsequent fine grinding and/or sieving.

The entire method comprises the three steps selection and preparation of the raw materials, mechanical partial deoiling as well as extraction, and is shown schematically in FIG. 1. A further example of embodiment can be seen in FIG. 3.

1. Selection and Preparation of the Raw Materials:

The hulls are largely separated by means of a suitable dehulling technology so the residual hull content related to the obtained dehulled seed fraction is around 1% by weight. Particularly advantageously, easy to dehull raw material types and species are selected, more particularly edible seeds instead of oil-type seeds. In this patent application the details of the residual hull content relate to the total mass of the seed fraction as obtained immediately after dehulling.

2. Mechanical Partial Deoiling

Pressing the sunflower seeds with a low residual hull content through screw presses, controlling the temperature/cooling to under 80° C., preferably under 60°, more preferably under 50° C. In this way Maillard reactions and other protein modifications are reduced, as are reactions of other secondary substances with proteins, e.g. polyphenols.

Pressing takes place to a residual oil content of 10-35%, preferably 17-25% by weight. Pressing is carried out with a press shape or nozzle which allows the formation of stable oil cakes, e.g. in the form or pellets or strands, with are nevertherless not pressed together too hard and exhibit a certain porosity.

Figure 2:
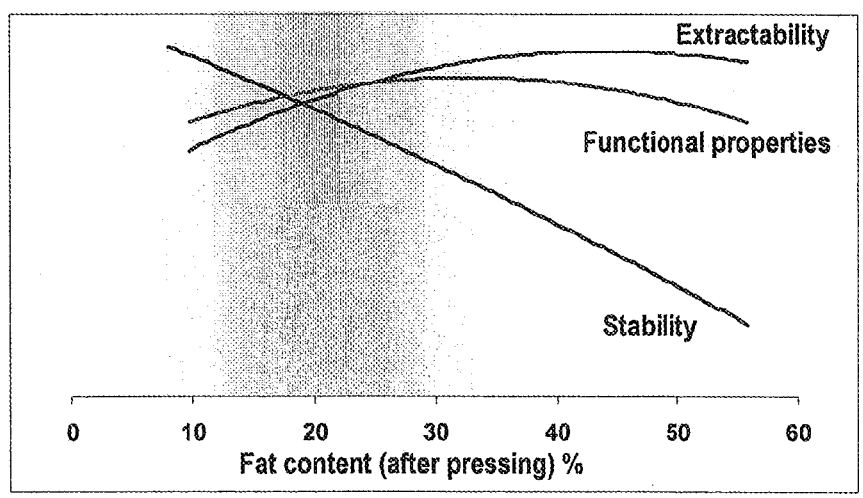
FIG. 2 shows a view for determining the optimum degree of pressing in terms of mechanical stability and maintenance of the extractability of the oil cakes and functional properties of the resulting preparations.

With suitable selection of the pressing configuration (in particular the nozzle shape) the pellets hold together surprisingly well at the above residual oil contents, and in spite of the low hull content allow further deoiling with a solvent with subsequent comminution. The inventors have discovered that due to the above mechanical partial deoiling in screw presses good seed maceration and an advantageous product form for extraction are achieved, so that further communition or preparation for the subsequent extraction stages can be dispensed with. It was found that the achieved residual oil content is linked to the mechanical properties in that there is an optimum degree of deoiling at which the oil cake properties are ideal, as can be seen in FIG. 2. In this example the optimum degree of deoiling lies at a residual oil content of around 17-20% by weight.

Particularly beneficially for the efficiency of the further extraction step, mechanical partial deoiling is carried out until there is fat or oil content in the dehulled sunflower seeds at which a stable oil cake is obtained through pressing which has a thickness in the range 0.2 to 4 cm, preferably in the range between 0.5 and 2 cm.

Pressing is carried out with a pressing shape or nozzle which allows the formation of stable oil cakes, e.g. in the form of pellets or strands. Particularly advantageously a screw press with a round-hole matrix or a nozzle or an extruder with a round nozzle are used for pressing, so that the obtained pressed products are in the form of strands with a round cross-section of 5-20 cm in diameter. By selecting a suitable degree of pressing, in which the residual fat content is in a range between 12 and 25%, pressed products with a porosity which is still sufficient for extraction and with good stability are obtained. Pressed strands with a breaking strength of between 2 and 10 $N/mm^2$, ideally between 4 and 9 $N/mm^2$ at a bulk weight of between 300 and 500 $kg/m^3$ are obtained.

3. Extraction of the Prepared Seeds or Oil Cake Pellets

Preferably further extraction takes place though a combination of at least two extraction solvents of different polarity in such a way that obtained hydrophilic secondary substances are extracted before, with or after the oil. Below, all pure fluids and solutions (e.g. organic solvent or water and aqueous solutions or supercritical gases) and fluid mixtures which can be used for extraction are designated as extraction solvents. At least two changes in polarity are set through the succession of the extraction solvents. This can be set to occur suddenly or continuously through the previously present extraction solvent being mixed with or displaced by the following one. All solvents and mixtures therefore approved in accordance with food legislation can be considered, more particularly water, acids, alcohols, esters, ketones, e.g. acetone, ethers, alkanes such as n-hexane and iso-hexane, the polarity or solubility in water decrease in said sequence (from hydrophilic to lipophilic), as well as supercritical fluids and gases, e.g. $scCO_2$ (supercritical $CO_2$), which at the most critical point tends to be lipophilic and the polarity of which can be changed further by further increasing the pressure in the direction of hydrophilic as well as increasing the temperature.

Thus, for example, the following steps can be carried out, whereby the sequence of the hydrophilic and lipophilic steps is preferably selected in such a way that that the overall extraction produces a maximum yield (i.e. at least 90% of the yield achievable with the pure solvent).

Extraction of moderately hydrophilic secondary substances, more particularly phenolic acids and aroma substances through alcohol, preferably isopropanol, ethanol or methanol, in a concentration at which the proteins are not dissolved or only to small extent. For this an alcohol concentration of more than 60%, preferably between 60 and 80% is set (v/v concentration of the alcohol in the extraction solvent). $scCO_2$ can also be used as a solvent, preferably at a temperature between 40 and 80° C. and at a pressure of over $300 \times 10^5$ Pa, preferably in the range $350-800 \times 10^5$ Pa, whereby with increasing pressure is exhibits more hydrophilic properties.

Extraction of lipophilic components with a lipophilic solvent up to complete deoiling to a residual oil content of at most 5% (Büchi method according to Caviezel). For example hexane, pure alcohol (≥95%) or $scCO_2$ can be used as lipophilic solvents at temperature in the range 31-60° C. and at a pressure in the range $74-350 \times 10^5$ Pa. In this way oil, phospholipids and other lipophilic components such as carotinoids are extracted in particular.

If required, repetition of the first extraction after the second extraction.

The lipophilic extract can, if required, also be carried out before the hydrophilic extraction.

Advantageously the polarity of the extraction solvent is changed through the present residual water after the preliminary treatment, more particularly after mechanical preliminary deoiling and/or during oil extraction, so that during the extraction process with a single added solvent different polarities of the actual extraction mixtures are brought about.

When using supercritical gases, more particularly supercritical carbon dioxide ($scCO_2$) the polarity can be changed just by altering the pressure and temperature so that the addition of a further solvent is not necessary. Through successive displacement of the water bonded to the raw material the polarity can be changed more or less continuously.

Particularly advantageously the more hydrophilic polarity is set first so that the residual water bonded in the raw material can be used to modify the polarity in such a way that hydrophilic substances can be extracted without the further addition of water or with little added water. Surprisingly, during the transition to the lipophilic phase this simultaneously brings about a reduction in the residual water content so that lipophilic extraction is favoured. Due to the removal of the water before or during the first extraction, the otherwise usual drying before deoiling can be dispensed with. Normally conditioning would be necessary after pressing as with an increasing relative water content in the oil cake deoiling with lipophilic solvents would be made more difficult due to the reduced oil content and resulting lower overall mass.

Particularly advantageously the first solvent or residues of the first solvent, e.g. the alcohol or alcohol-water mixture, is displaced by the next, second solvent.

It may be necessary to displace the water completely with alcohol to avoid the negative influences of water in the following extraction. The alcohol concentration is increased in the first extraction until the alcohol can then be dissolved by the more lipophilic solvent. Selective separation at various pressure stages using $scCO_2$ allows the alcohol phase to be largely separated. Due to the water contained in the raw material or the added water or other co-solvents, the solution properties can be modified further so that moderately polar substance can be obtained. By combining high pressure ($>500\times10^5$ Pa) and a temperature between 40 and 60° C. better extraction rates of the phenolic acids and secondary oil substances are achieved. The introduction of the second solvent (apart from water) into the supercritical phase can also improve the extraction of phenolic acids and other secondary substance, such as pigments and aromatic substances. Particularly advantageously the extraction conditions with $scCO_2$ are set so that both water and alcohol residues are successively displaced from the raffinate and dissolving at high temperatures then becomes superfluous. In this way subsequent drying of the raffinate can be dispensed with even when using water as an entrainer/modifier.

When using aqueous alcohol extraction using the extraction solvent is carried out in several extraction steps, whereby at least in the last transition from one to the next extraction step the alcohol content in the extraction solvent is increased to a maximum, i.e. up to the concentration of the aqueous azeotroph, e.g. 96% (v/v) in the case of ethanol, so that the alcohol concentration in the extraction mixture increases to over 90% (v/v). This allows particularly gentle subsequent drying due to the reduction in the proportion of residual water to be removed, which evaporates more slowly and at a higher temperature than alcohol.

Of course further extraction (after the mechanical partial deoiling) can also be carried out with only one solvent, more particularly hexane, in order to obtain the deoiled flour containing protein.

The extraction is carried out under such conditions that the proteins are not, or only slightly dissolved and the protein are not or only minimally damaged and no or only few undesirable chemical reactions occur, such as the Maillard reaction or Michael addition of phenolic acids (e.g. measurable as max. 20% less free phenolic acids and/or available lysine and/or reproducible sugar and/or max. 10% lysinoalanine or Maillard products). Furthermore, at the set temperature no thermally caused aroma changes to the extracted material occur. For this the temperature is held below 80° C., better at 60° C., ideally below 40° C. If hexane deoiling is being carried out complete desolventisation can be improve by applying a vacuum (100-800 hPa, preferably 200-500 hPa, particularly preferably 200 hPa), whereby desolvent-isation is made possible up to max. 60° C. In the case of other solvents the application of vacuum is also advantageous in order to allow desolventisation at lower temperatures.

It is shown that in the case of sunflower seed proteins defined denaturing of 5%-40%, advantageously between 10% and 30% (e.g. measurable as a deviation of max. 30%, better 20%, even better 10% with regard to functional properties such as protein solubility, max. 30% greater protein denaturing, measurable with thermoanalytical method such as DSC)—related to the proteins of the starting product of the proposed methods is particularly advantageous for obtaining a broad application spectrum.

The extraction sequence can also take place inversely, if, for example, the extract substances are to be used for specific applications. Full deoiling in the first step can be of advantage in terms of obtaining the secondary substances as functional food additives or for cosmetic or technical applications. Particularly advantageous is the combination of deoiling with supercritical $CO_2$, subsequent (aqueous) alcoholic solvent extraction and final $scCO_2$ treatment for the simultaneous desolventisation and drying to stable finished products. The combination is preferably set up so that all extractions are carried out consecutively in one container and only the solvents, temperatures and pressures are changed.

Surprisingly the valuable protein and phenol fractions can be simultaneously obtained and used for various food applications. The secondary substances contained in the alcohol can be used directly for high-value application or processed further. Also of particular advantage is the use of $scCO_2$ before or during the extraction of polyphenols, as through the displacement of oxygen oxidation is prevented.

Surprisingly it is also shown that when using alcohol the depletion of phospholipids is improved vis-à-vis pure hexane extraction, which further improves the sensory quality of the deoiled flour.

It has also been show that the protein fraction can be obtained free of thermally-caused aromatic substances and use in foods can be improved through sensory-neutral protein products. At the same time the functional properties of the proteins are retained.

Through the above-described production method a sunflower protein preparation can be obtained which, compared for example with protein isolates obtained through aqueous fractionation and laborious isolation methods, is characterised by a balanced nutritional value profile and technofunctional spectrum. Without further processing, in order, for example, to achieve the high protein content of a protein isolate, it is also suitable as a food or animal feed additive. Surprisingly, even though it is not a protein isolate, the protein preparation has the technofunctional properties of a protein isolate. It has a neutral, light colour and is largely free of sensorily undesirable and anti-nutritive secondary substances. More particularly the sunflower protein concentrate has almost no smell or taste of its own.

It is particularly surprising that even the deoiled sunflower protein flour (SFPF) has a very appealing colour and very distinct functional properties and is suitable for numerous food and animal feed applications.

In the following, for the quantitative characterisation of the produced protein preparations the following determination methods are used:

Protein content:
The protein content is defined as the content calculated from the determination of nitrogen and its multiplication by a factor of 6.25. The protein content can be indicated, for example, in percent related to the dry mass (TS).

Colour:
The perceived colour is defined by means of CIE-L*a*b* colour measurement (cf. DIN 6417), whereby the L* axis indicates the brightness, where black is 0 and white is 100, the a* axis describes the red and red portion and the b* axis the blue and yellow portion.

Protein solubility:

The protein solubility is determined by mean of determination methods according to Morr et al. 1985 (see the journal article: Morr C. V., German B., Kinsella J. E., Regenstein J. M., Van Buren J. P., Kilara A., Lewis B. A., Mangino M. E. "A Collaborative Study to Develop a Standardized Food Protein Solubility Procedure". Journal of Food Science, vol. 50 (1985) pages 1715-1718). For this a protein preparation is suspended in a 0.1 M NaCl solution at room temperature to a mass-volume ratio of 1:25 to 1:50 (w/v) (i.e. 1-2 g of the protein preparation to 50 ml solution) and using 0.1 M HCl or NaOH solution is kept for approx. minutes at a pH value of pH 7 and stirred at approx. 200 rpm and insoluble sediment is then centrifuged off at 20 thousand times gravitational acceleration (20,000 g). The protein solubility can, for example, be given in percent, where a protein solubility of x % means that x % of the protein present in the preparation is found in the clear supernatant if said method is used.

Hydration

The hydration capacity is defined by means of determination methods (hereinafter referred to as AACC determination methods) as set out in: American Association of Cereal Chemists, "Approved methods of the AACC" $10^{th}$ edition, AACC. St Paul, Minn., 2000b; Method 56-20. "Hydration capacity of pregelatinized cereal products". The hydration capacity can be indicated in ml/g, i.e. milliliters of bound water per gram of preparation, and in accordance with the AACC determination method is determined via the weight of water-saturated sediment minus the weight of the dry preparation after mixing approximately 2 g protein preparation with approximately 40 ml water for 10 minutes and centrifuging at 1000 g for 15 minutes at 20° C.

Oil binding

The oil binding capacity is defined in accordance with determination methods (hereinafter referred to as fat binding determination methods) as set out in: Ludwig I., Ludwig E., Pingel B. "A micromethod for determining the fat binding capacity" Nahrung/Food 1989, 33 (1), 99.

The oil binding capacity can be indicated in ml/g, i.e. milliliters of bound oil per gram of preparation and in accordance with the above determination method is measured as the volume of oil-binding sediment after mixing 1.5 g protein preparation with 15 ml maize seed oil for 1 minute and centrifuging at 700 g for 15 minutes at 20° C.

Emulsifying capacity:

The emulsifying capacity is determined by means of a determination method (hereinafter referred to as the conductivity measuring method), in which maize seed oil is added to 100 ml of a 1% suspension of the protein preparation at pH 7 until phase inversion of the oil in water emulsion. The emulsifying capacity is defined as the maximum oil absorption capacity of this suspension, determined via the spontaneous decrease in conductivity at phase inversion (cf. the journal article by Wäsche A, Müller K, Knauf U. "New processing of lupin protein isolate and functional properties", Nahrung/Food, 2001, 45, 393-395) and can be indicated in ml oil/g, i.e. milliliters of emulsified oil per gram of protein preparation.

Foam activity

The foam activity is indicated in percent, measured as the increase in volume of a 5% solution, pH7 when whisked at setting 3 (591 rpm) for 8 minutes in a Hobart 50N standard food processor (steel container with a content of 5 liters) with a whisk (wire whisk).

Foam density

The foam density is indicated in g/ml, i.e. the mass of the foam per unit of volume and is measured after whisking of 5% solution, pH7 at setting 3 (591 rpm) for 8 minutes in a Hobart 50N standard food processor (steel container with a content of 5 liters) with a whisk (wire whisk).

Foam stability

The foam stability in indicated in percent, measured as the reduction in volume of 100 ml foam within one hour after whisking of a 5% solution, pH7 at setting 3 (591 rpm) for 8 minutes in a Hobart 50N standard food processor (steel container with a content of 5 liters) with a whisk (wire whisk).

Fat content

The fat content determined after sample maceration and saponification of the fatty acids, e.g. in accordance with the Caviezel method (described in DGF "Method of Caviezel" DGF K-I 2c (00). In the Deutsche Gesellschaft für Fettwissenschaft e.V. Münster. DGF standard methods, $2^{nd}$ edition, Stuttgart: WVG 2004).

For comparative purpose the following commercially produced products were used:

Pea protein isolate Pisane® (produced by Cosucra)
Soya protein isolate SUPRO® EX33 (produced by DuPont)
Sodium caseinate (spray dried), FN5S by Rovita With the production method in accordance with the invention protein preparations with the following properties can be produced from sunflower seeds:

Appearance:
  In pourable form, e.g. as flakes, granulate, powder or in the form of other particles
  The colour is white to cream-coloured, light grey or light yellow, possibly with a proportion of darker coloured particles of max. 5% w/w, preferably below 2% w/w. The lightness $L^*$, determined in accordance with CIE-$L^*a^*b^*$ colour measurement produces a value of at least 70, $L^*>=70$. The following are typical examples of value for $L^*$, $a^*$ and $b^*$
  $L^*>=80$, $-5<a^*<+5$, $-5<b^*<+20$; preferably
  $L^*>=85$, $-3<a^*<+3$, $-2<b^*<+15$, particularly preferably
  $L^*>=90$, $-1<a^*<a^*$, $0<b^*<+10$.

Composition
  The protein content is less than 90% in the dry mass (TS), preferably less than 80% related to TS. Typically the protein content is between 50 and 70 related to TS.
  Total bulk material content is between 10 and 40% related to TS, preferably between 10 and 30% related to TS.
  The fat content, determined for example by gravimetric determination after Soxhlet extraction, is less than 3% related to TS, preferably less than 1%
  The total sugar content is under 15% related to TS, preferably under 5%, particularly preferably under 2%.
  Content of undesirable, more particularly antinutritive substances:
    Phytinic acid content under 5%, related to TS, preferably under 2%, particularly preferably under 1%.
    Raffinose content under 5% related to TS, preferably under 2.5%, particularly preferably under 0.5%
    Phenolic acid content (determined a chlorogenic acid) under 5% related to TS, preferably under 2%, particularly preferably under 0.5%.
  Lignin content under 6% related to TS, preferably under 4%, particularly preferably under 3%.

In general the protein as well as lignin content in sunflower protein flour (SFPF) is lower than in sunflower protein concentrate (SFPC) produced therefrom, while the content of fat, sugars and phenolic acids is higher in the SFPF than in the SFPC.

Technofunctional Properties:

Protein solubility:

The protein solubility determined in accordance with the PNG determination methods is greater than 30%, preferably greater than 400. Typically the protein solubility is in the range 30-60%.

Hydration

The hydration, determined in accordance with the AACC determination method is at least 2 ml/g, preferably at least 3 ml/g. Comparative measurements show that the hydration of the preparation is at least 30% of the hydration of Pisane® determined in accordance with the AACC determination method.

Oil binding:

The oil binding, determined in accordance with the fat binding determination method is at least 1 ml/g, preferably at least 4 ml/g. Comparative measurement show that the oil binding is at least 100% of the oil binding of Pisane® or of Supro® EX33, determined in accordance with the same method.

Emulsifying capacity:

The emulsifying capacity determined in accordance with the conductivity measurement method is at least 400 ml oil/g, preferably at least 500 ml oil/g. Comparative measurements show that the emulsifying capacity is at least 40% of the emulsifying capacity of sodium caseinate FN5S, determined in accordance with the same method.

Foam forming properties:

Foam activity

The foam activity is at least 1000%. Comparative measurements with fresh hen egg white whisked for 3 minutes at setting 3 in a Hobart 50N standard food processor with a whisk show that the foam activity of the protein preparation is at least 50% or even at least 60% of the foam activity of hen egg white.

Foam density:

The foam density is in the range from 80 to 110 g/l. Comparative measurements with fresh hen egg white whisked for 3 minutes at setting 3 in a Hobart 50N standard food processor with a whisk show that the foam density is in the range 80-110% of the foam density of beaten hen egg white.

Foam stability:

The foam stability is at least 80%, preferably at least 90%. It typically corresponds to at least 90% of the foam stability of beaten hen egg white, measured the decrease in volume of 100 ml beaten hen egg white within one hour after whisking for 3 minutes at setting 3 in a Hobart 50N standard food-processor with a whisk.

Sensory Properties:

In addition to the light colour, the protein preparation, particularly in the form of the SFPC, is essentially free of smell and neutral in taste. More particularly it lacks the inherent plant and seed aromas. Thus, there is therefore no bean-like or grassy smell and taste, and no bitter taste is perceived.

Sensory tests in which trained testers compare a certain taste or aroma impression of the protein preparation and a suitable reference substance and evaluate it on a scale of 1 to 10 (1=not perceptible, 10=strongly perceptible), whereby the reference substance is selected so that the taste or aroma impression to be tested is evaluated with at least an 8, show that the protein preparation achieves a value of 3 or less (typically a value of 1).

Examples of taste or aroma impression to be tested are:

Bean-like taste in comparison with soya beans

Green to grassy taste in comparison with green peppers or green peas

Bitter taste in comparison to a 0.1% aqueous caffeine solution.

The colour, inherent taste and inherent smell of the protein preparation are such that when incorporated into food products and animal feeds there is no significant change to the appearance, smell or taste of the finished preparation which could be evaluated negatively with normal statistical methods.

Sensory tests show that the change to the taste and aroma brought about in a food product through the use of the protein preparation is restricted to such an extent compared with the food product without the protein preparation that a trained tester can determine a change in the above taste and aroma features of a maximum of 3 steps, better maximum 1 (almost no longer perceivable change) of a scale of 1-10.

In the proposed method through the use of alcohol or alcohol solution mixed with the seeds' own water the majority of plant's aromatic substances and other secondary plant substances such as phenolic acid are removed. In this way light, discoloration-stable and almost smell-free and taste-neutral flour are obtained.

Surprisingly the protein content of the raffinate/raffinate/flour can be increase to proportions of greater than or equal to 60% by the joint extraction of other low-molecular components, more particularly the contained sugars, so that without further processing stage high-quality stable protein concentrates are obtained.

In the alcohol, aqueous or water-alcohol phase a mixture of sugars/oligosaccharides and secondary plant substances such as phenolic acids can occur. Particularly advantageously the sugar substances can be used as carrier substance for the phenolic substance, e.g. during subsequent drying, for the production of another form of application. Through selective adsorption, crystallisation or precipitation the two fractions can be purified further or separated in order to be able to use both fractions separately.

The inventors have also recognised that there are particular advantages to extraction with $scCO_2$ in the further wet processing of the deoild grist/flours due to the reduced quantity of troublesome secondary substances, as the $CO_2$ contained in the grist also has a stabilising effect in subsequent processing as oxidation processes are restricted.

A further advantage is seen if the obtained preparations are packed directly after $scCO_2$ treatment. Surprisingly they are then directly protected against oxidation without the supply of additional protective gas. Partial ventilation or combination with other protective gases can nevertheless be of advantage.

It was also found that the functional properties of the protein preparations can be modified by adjusting the particle size. Through appropriate fine comminution or fractionation by particle size or particle density of the sunflower protein flour or concentrate the hydration or emulsifying capacity can be specifically adjusted in order to meet different requirements. Particularly advantageously a particle size of ≤500 μm is set or a fraction with a particle size of ≤500 μm separated.

In accordance with the method according to the invention, using a minimal amount of water the production of high-quality sunflower protein preparations is possible which surprisingly have properties similarly as good as protein isolates, even though they have a lower protein content. With the aid of the described technology sunflower seeds are almost completely fractionated into nutritionally and technofunctionally valuable food product ingredients and fractions for energy and technical use, whereby the protein yield is particularly high.

It was also found that the obtained alcoholic solution containing sugar can be used directly for fermentation to bioethanol.

The inventors have also found that the oil which is obtained through non-polar reaction and contains hexane, can be used without further processing for adding to or producing biodiesel, or directly as fuel.

In a further advantageous embodiment of the method the extractions are arranged consecutively so that with the supercritical $CO_2$ the residual alcohol bound in the grist can be simultaneously extracted so that following distillation or purification stages can be dispensed with. The inventors have found that the oil which is obtained through non-polar extraction and contains residues of alcohol, is surprisingly well suited to further processing into biodiesel and can be used directly in a process based on the enzymatic re-esterification of fat with alcohol. In a particularly advantageous manner any alcohol portions entrained into the oil are not removed, but remain contained in it and are used in further processing of the oil to biodiesel after the re-esterification process.

EXAMPLES OF EMBODIMENT

Example 1

Sunflower Seed Protein Concentrate from Alcoholic Extraction from Deoiled, Dehulled Sunflower Seeds Dehulled edible seeds with a purity of 99.8%, i.e. a hull content of <0.1% were deoiled in a screw press with a 5 mm diameter nozzle at a temperature of approx. 40° C. (±5°) to a residual fat content of 23% and the obtained strand-like pressed products were deoiled with hexane in a Soxhlet for 36 hours and dried at room temperature to remove the hexane residues. The thus obtained hexane-deoiled sunflower grist from dehulled edible salts containing phenolic acid was extracted with methanol (95%) in the Soxhlet whereby the alcohol concentration increased from initially approx. 80% (v/v) to approximately 95% through extraction of the water. The temperature of the oil bath was approximately 85%, the extraction temperature was between 20° C. (cooler) and maximum 65° C. (boiling point of methanol=65° C.). After 12 cycles the extraction was ended after several cycles no longer showed a yellow colouring of the extract.

The thus obtained sunflower protein concentrate is a fine, light-coloured powder with a protein content of >60%. The composition is shown in the following table:

| No. | Sample name | Dry mass (TS) % | Protein in TS % | Fat in TS (Büchi) % | Ash in TS % | Phenolic acids in TS % | Emulsifying capacity ml/g |
|---|---|---|---|---|---|---|---|
| 1 | Sunflower seed flour (grist from dehulled sunflower seeds) | 90.4 | 61.1 | 3.6 | 7.5 | 0.50 | 510 |
| 2 | Sunflower protein concentrate (from 1) | 87.8 | 76.5 | 1.5 | 8.6 | 0.01 | 210 |
| 3 | Sunflower protein isolate (from 2) | 89.1 | 96.2 | 0.29 | 4.20 | 0.00 | 675 |

The protein concentrate is low in plant-inherent aroma components. The colour of this sunflower protein flour and concentrate with a low hull content is particularly appealing/neutral and in accordance with CIE L*a*b* has the following values:

| No. | | L* | a* | b* |
|---|---|---|---|---|
| 1 | Sunflower seed flour | 90.0 | 0.47 | 6.33 |
| 2 | Sunflower seed protein concentrate (from 1) | 86.8 | 0.18 | 8.11 |
| 3 | Sunflower seed protein isolate (from 2) | 73.0 | 1.22 | 10.94 |

The sunflower flour previously contained approximately 0.5% caffeic acid derivatives, detected with HPLC (electrochemical detection) and quantified by way of photometric determination. The extracted sunflower flour, hereinafter referred to as sunflower protein concentrate, only contained traces of chlorogenic acid, i.e. at the detection limit of 0.011. Accordingly 90% of the phenolic acids were extracted, identified and quantified as caffeic acid derivatives. The extracted quantity was detected in full in the extract. The dry mass loss (TS) was 24%. Small proportions of the extracted dry mass consisted of protein, fat and mineral materials. In addition to phenolic acids mainly sugar, oligosaccharides and bulk materials were contained, 63% of which were extracted of which oligosaccharides such as raffinose make up a maximum of 30% in the case of full extraction. Surprisingly therefore, other secondary plant substances, in particular phytinic acid, pass into the extract.

The phenolic acids were almost completely extracted from the grist and could be detected in the extract. The mineral content of the grist increased slightly through the treatment with methanol, whereas other secondary substances were removed. The extraction with methanol led to extensive depletion of troublesome secondary substances, in particular the phenolic acids as well as secondary oil substances. The protein content was increased to over 60% so that a colour-stable protein concentrate can be obtained or a follow wet production of high-value protein isolates is not disrupted by polyphenols (see colour of the protein isolate, table).

Example 2

Pressing of Dehulled Sunflower Seeds

Dehulled edible seeds were deoiled at 40-50° C. with a screw press with three different nozzles having a diameter of 6, 5 and 4 mm respectively. The obtained oil cakes differed in terms of fat content as well as their structure and colour (table 2-1). The fat content was determined with two methods whereby the Büchi method (according to Caviezel) indicates the total fat content and the Soxtherm method determines the extractable portion.

| Sample designation | Dry mass (TS) % | Protein in TS % | Fat in TS (Büchi) % | Fat in TS (Soxtherm) % |
|---|---|---|---|---|
| Dehulled sunflower seeds | 94.7 | 25.2 | 55.9 | 52.2 |
| Oil cake 1st nozzle 6 mm | 92.4 | 37.9 | 36.3 | 34.5 |
| Oil cake 2nd nozzle 5 mm | 92.3 | 37.9 | 35.3 | 33.4 |
| Oil cake 3rd nozzle 4 mm | 90.3 | 52.8 | 9.6 | 6.6 |

During pressing with the narrowest nozzle the pressure in the press increased considerably so that a very firm oil cake with a low fat content of approximately 10% was achieved. However, under these conditions the oil cake was darker, which assumes oxidation or a Maillard reaction. In the gentler pressing with a larger nozzle of 5/6 mm the residual fact content was much higher at approximately 33 and 35% respectively. However this could be reduced to under 1% through subsequent extraction (table 2-1).

Determination of the functional properties resulted in an improvement in protein solubility as well as emulsifying capacity compared with the initial seeds in the latter two oil cakes, i.e. better cell breakdown and good porosity were achieved by the pressing. The porosity is lost with an increasing degree of pressing. In order to achieve optimum strength of the oil cake with good mechanical stability during the subsequent extraction the degree of pressing should on the other hand be as high as possible.

In addition to the nozzle geometry the pressing temperature also affected the degree of deoiling and structure of pressed products. The strength of the pressed products with a round cross-section was determined by means of Texture Analysers (TA) at radial pressure loading with 75 mm diameter stamp at a stamp speed of 1 mm/s. The maximum force used up to breakage of the pressed product was measured. The force was related to the loaded surface of 1 mm width and length of the pressed product under the stamp. The mean value of the breaking pressure was determined by means of 20 samples.

TABLE 2-2

| | Fat content | Mean value break pressure N/mm$^2$ | Pouring density kg/m$^3$ |
|---|---|---|---|
| Nozzle 5 mm, pressed at <40° C. | 35% | 0.58 | 310 |
| Nozzle 5 mm, pressed at <40° C. | 23% | 0.96 | 350 |
| Nozzle 5 mm pressed at 55-60° C. | 17% | 4.81 | 420 |
| Nozzle 8 mm pressed at 60-70° C. | 11% | 9.76 | 470 |

A very low residual fat content of 11% could also be achieved with a large nozzle with a diameter of 8 mm (table 2-2) if the temperature was increased up to 70° C. These pressed products exhibited a very high degree of mechanical stability, but had a higher pouring density and therefore lower porosity and were slightly darker in colour than the oil cake obtained at 40° C. When using lower temperatures under 60° C. an almost solid material, but with considerably higher porosity could be obtained (table 2-2), which exhibited only slight thermal damage and which could be very easily extracted. On the other hand at temperatures >70° C. distinct protein damage and strong discoloration could be determined.

It was found that with a degree of pressing of a residual fat content in the range from approximately 15% to 25% residual fat, oil cake pellets are obtained, which in spite of the absence of hulls exhibit good mechanical stability with still sufficient porosity, so that without further structuring or comminution, complete deoiling is possible in the subsequent extraction. Surprisingly, even after deoiling in spite of the loosening of the structure associated with removal of the oil, the pellets still exhibit sufficient mechanical stability to be subjected to extraction with another solvent and thereby depletion of non-protein substance without falling apart. Due to this porous structure they exhibit very favourable extraction properties for further extraction, i.e. with alcoholic solvent. In this way structuring or comminution before extraction, which otherwise normally has to be carried out, can be dispensed with.

Depending on the configuration and geometry of the pressing device the optimum degree of pressing is achieved with a residual oil content of approximately 15% to 25% (cf. FIG. 2). It was found that even at temperatures below 60° C. adequate compaction of the pressed products is achieved and at the same time the functional properties and colour of the proteins are optimally preserved.

Overall, through pressing in which a certain residual fat content remains, the particles can be structured so that subsequent structuring or comminution, which is normally carried out to break up the oil cake before extraction, is no longer necessary. In addition to simplifying the process this also protects the oil cake so that, among other things, the functional properties of the protein and the colour of the end product can be improved.

Through the reduced degree of pressing the proteins are also protected and the functional properties of the protein preparation are better preserved. At the same time a particle form is produced which allows optimum extraction whereby the residual oil content after deoiling can be reduced further. This too contributes to an improvement in the colour of the protein preparation.

Example 3

Sunflower Seed Flours and Protein Concentrates Obtained Through Deoiling and Extraction Hull-Free Oil Cakes with Hexane, scCO$_2$ and Ethanol Production:
1. Dehulling of the sunflower seeds and separation into a seed and hull fraction and use of the seed fraction with a hull content of max. 0.5% (w/w)
2. Mechanical partial deoiling to a residual fat content of approximately 36% by pressing as in example 2.
3. Deoiling of the sunflower oil cake a) with isohexane in a percolator at temperatures of max. 60° C. of b) extraction with supercritical CO$_2$ in a pressurised contained (for settings see table below).
4. Extraction of the oil cake from 2 or the protein flour form 3a with ethanol and/or hexane in a Soxhlet apparatus (for settings see table below).
5. Displacement of the hexane after extraction 3a with superheated hexane vapour in a vacuum (<500 hPa).
6. Displacement of further hexane from 5 with superheated water vapour a vacuum (<500 hPa).

7. Removal or solvent residues from 6 through heating to 60° C. in a vacuum (<500 hPa). The thus obtained raffinate is then called protein flour.
8. Removal of the solvent after extractions 4 in an air flow at room temperature in order to obtain protein concentrates.
9. Evaporation of the alcohol and drying of the raffinate obtained in process step 8 in a rotation evaporator in order to obtain sunflower protein concentrate.
10. Milling of the sunflower protein flour and concentrates from step 3b, 7 or 9 in a pin mill with a 0.5 mm sieve insert in order to obtain the sunflower protein preparations as a find powder.
11. Use of the protein flour and protein concentrates with our without prior or subsequent comminution.

The pellets from the screw press (5 mm nozzle in example 2) were then deoiled in two different ways, 1. with hexane (deoiling and desolventisation at temperatures below 60° C.) and 2. with supercritical $CO_2$. With hexane complete deoiling was achieved, and extraction with $CO_2$ at $800 \times 10^5$ Pa was also almost completed, but at $285 \times 10^5$ Pa around 20% less oil was extracted (50° C., 100 kg/kg $CO_2$). An examination of the acidic number of the oils from both extraction processes showed no underlying differences. It also showed that the pellets are very well suited to extraction without further comminution or preparation.

TABLE 3-1

| No. | Sample designation and production | Dry mass (TS) % | Protein in TS (N × 6.25) % | Fat in TS (Büchli) % | Ash in TS % | EC |
|---|---|---|---|---|---|---|
| 1 | Oil cake | 92.3 | 42.3 | 35.3 | 4.6 | 505 |
| 2 | Sunflower seed flour hexane deoiled at <60° C. (from 1) | 90.8 | 63.6 | 3.0 | 7.7 | 510 |
| 3 | Sunflower seed flour scCO$_2$ extracted at 50° C. 285 × 10$^5$ Pa (from 1) | 94.2 | 58.6 | 10.7 | 6.7 | 598 |
| 4 | Sunflower seed flour scCO$_2$ extracted at 50° C. 800 × 10$^5$ Pa (from 1) | 93.6 | 62.7 | 3.8 | 7.7 | 513 |
| 5 | Sunflower seed protein concentrate extracted with ethanol (from 1) | 92.4 | 58.9 | 15.7 | 6.9 | 280 |
| 6 | Sunflower seed protein concentrate extracted with ethanol (from 2) | 90.9 | 69.0 | 0.4 | 8.4 | 380 |
| 7 | Sunflower seed protein concentrate extracted with ethanol and deoiled with hexane, flow transition (from 5) | 90.4 | 70.3 | 0.3 | 8.4 | 285 |
| 8 | Sunflower seed protein concentrate extracted with ethanol, dried and then deoiled with hexane (from 5) | 90.3 | 69.0 | 0.2 | 8.2 | 285 |

Properties

The thus obtained sunflower protein flours and concentrates have a protein content of at least 50% (N×5.6) and a further composition as well as functional properties as set out in the following table. The thus obtained sunflower protein concentrates (no. 6-8) are free of inherent sunflower aroma components. The flour (no. 2) still had a certain inherent nutty sunflower taste. After simple milling and sieving (<263 mm) it was used to emulsify an egg-free salad mayonnaise which was comparably as homogeneous and stable as with a plant protein isolate and was assessed as good in sensory terms.

The colour of the hull-free sunflower protein flour and the sunflower protein concentrates is particularly appealing, i.e. neutral, and has the following values in accordance with CIE-L*a*b*:

TABLE 3-2

| No | Sample designation and production the same preparations as in table 3-1 | L* % | a* % | b* % |
|---|---|---|---|---|
| 1 | Oil cake | 70.5 | 1.95 | 12.75 |
| 2 | Sunflower seed flour hexane deoiled at <60° C. (from 1) | 89.21 | 0.59 | 6.48 |
| 3 | Sunflower seed flour scCO$_2$ deoiled extracted 50° C., 285 × 10$^5$ Pa (from 1) | 88.4 | 0.49 | 7.49 |
| 4 | Sunflower seed flour scCO$_2$ deoiled extracted 50° C. 800 × 10$^5$ Pa (from 1) | 89.3 | 0.31 | 6.79 |
| 5 | Sunflower seed protein concentrate extracted with ethanol (from 2) | 88.0 | −0.0 | +7.8 |

Example 4

Sunflower Seed Protein Flour from Deoiled, Dehulled Sunflower Seed with Properties Modified Though Adjusting the Particle Size In this example modification of the functional properties of the sunflower protein preparation with subsequent particle size preparation was investigated.

Production
1. Dehulling of the sunflower seeds and separation into a seed and hull fraction.
2. Mechanical partial deoiling to a residual fat content of approximately 36% by pressing, see example 2.
3. Deoiling of the sunflower oil cake with isohexane in a percolator at temperatures of max. 60° C.
4. Displacement of the hexane with superheated hexane vapour in a vacuum (<500 hPa).
5. Displacement of further hexane with superheated water vapour in a vacuum (<500 hPa)
6. Removal of solvent residues through heating to 60° C. in a vacuum (<500 hPa). The thus obtained raffinate is then called protein flour.
7. Inspection, sieving and/or milling of the protein concentrate in a pin or hammer mill in order to obtain fractions with a different particle size distribution and in this way modify the functional properties.
8. Use of the protein flours and protein concentrates with our without previous or subsequent comminution.

The deoiled flour (no. 2) was only sieved (<263 mm) and used directly for emulsifying an egg-free salad mayonnaise which was comparably as homogenous and stable as one with a plant protein isolated. The taste and the texture could be improved further if the flour was milled.

Through processing in terms or particle size as carried out in the last step 7, the functional properties of the sunflower seed protein preparations could be changed. To reduce the particle size, in addition to pure milling visual selection of sieving, possibly in conjunction with milling were used. With decreasing particle the hydration tended to increased, in the case of the sunflower protein concentrate also the emulsifying capacity, whereas the oil binding capacity decreased slightly or hardly changed. The preparations with a homogenous particle size distribution exhibit greater hydration. Shown as being particularly advantageous for increasing the hydration was a combination of fractionation and comminution. Overall it is possible to modify the functional profile by way of specific processing of the particle size distribution.

The invention claimed is:

1. A protein preparation comprising dehulled sunflower seeds which have been mechanically deoiled through pressing which have the following characteristics:
    a) a protein content of less than 80% in relation to the dry mass of the preparation;
    b) a hull content of less than or equal to 5% in relation to the dry mass of the preparation;
    c) a hydration determined in accordance with the American Association of Cereal Chemists determination method of at least 2 ml/g dry mass of the preparation;
    d) an oil binding capacity determined in accordance with the fat binding determination method of at least 1 ml/g;
    e) a total dietary fiber content of between 10% and 40% in relation to the dry mass of the preparation; and
    f) a lightness (L*) of at least 70 determined in accordance with CIE-L*a*b* color measurement, wherein the values for a* and b* in accordance with CIE-L*a*b* color measurement are in the range $-5<a^*<+5$, $-5<b^*<+20$.

2. The protein preparation of claim 1, whereby the lightness (L*) is at least 80.

3. The protein preparation of claim 1 whereby the hydration of the protein preparation determined in accordance with the American Association of Cereal Chemists determination method is at least 3 ml/g and/or the oil binding capacity determined in accordance with the fat binding determination method, is at least 1 ml/g, and/or the emulsifying capacity, determined in accordance with the conductivity measuring method is at least 400 ml oil per gram of protein preparation.

4. The protein preparation of claim 1 or 3 whereby a protein solubility of the protein preparation in accordance with the Morr et al. determination methods is in the range of 30%-60%.

5. The protein preparation of claim 1 or 3 whereby the protein preparation has at least one of the following foam-forming properties: the foam activity corresponds to at least 50% of the foam activity of hen egg whites, the foam density corresponds to 50% to 200% of the foam density of beaten hen egg whites and the foam stability corresponds to at least 80% of the foam stability of beaten hen egg whites determined after whisking in a food processor.

6. The protein preparation of claim 1 or 3 whereby the protein preparation has a fat content which related to the dry mass is below 5% determined using the Caviezel method.

7. The protein preparation of claim 1 or 3 whereby the protein preparation has at least one of the following characteristics:
    a) a phytinic acid content, related to the dry mass, of under 10%;
    b) an oligosaccharide content, related to the dry mass, of under 10%; and
    C) a phenolic acid content, related to the dry mass, of under 8%.

8. A product comprising the protein preparation of claim 1 or 3 wherein the product is selected from the group consisting of a sunflower seed protein flour; a protein concentrate; a protein isolate with a protein content of at least 90%, related to the dry mass of the protein preparation; a food product; an animal feed; fish food; an ingredient for food products, an ingredient for animal feeds; and a cosmetic product.

9. The protein preparation of claim 1, whereby the lightness L* is at least 85.

10. The protein preparation of claim 1, whereby the lightness L* is at least 90.

11. The protein preparation of claim 1, wherein the values for a* and b* in accordance with CIE-L*a*b* color measurement are in the range $-3<a^*<+3$ and $-2<b^*<+15$.

12. The protein preparation of claim 1 wherein the values for a* and b* in accordance with CIE-L*a*b* color measurement are in the range $-1<a^*<+1$, $0<b^*<+10$.

13. The protein preparation of claim 1, wherein the oil binding capacity determined in accordance with the fat binding determination method is at least 4 ml/g and/or the emulsifying capacity, determined in accordance with the conductivity measuring method is at least 500 ml oil per gram of protein.

* * * * *